United States Patent [19]

Michael

[11] 4,102,564
[45] Jul. 25, 1978

[54] PORTABLE DEVICE FOR THE ACCURATE MEASUREMENT OF EYE MOVEMENTS BOTH IN LIGHT AND OBSCURITY

[76] Inventor: Henry L. Michael, 265 Riverside Dr., New York, N.Y. 10025

[21] Appl. No.: 660,030

[22] Filed: Feb. 20, 1976

[30] Foreign Application Priority Data

Apr. 18, 1975 [BE] Belgium ............................ 828128
Feb. 10, 1976 [BE] Belgium ............................ 164219

[51] Int. Cl.² .............................................. A61B 3/14
[52] U.S. Cl. ........................................ 351/7; 248/118; 297/392; 351/38
[58] Field of Search ............. 351/6, 7, 13, 16, 38; 248/118, 226 A; 297/391, 392, 406, 410; 357/17, 18

[56] References Cited

U.S. PATENT DOCUMENTS

| 3,379,885 | 4/1968 | Nork ............................. 351/7 UX |
| 3,473,868 | 10/1969 | Young et al. ....................... 351/6 |
| 3,594,072 | 7/1971 | Feather et al. ................ 248/118 X |
| 3,598,107 | 8/1971 | Ishikawa et al. ................ 351/6 X |
| 3,622,233 | 11/1971 | Blood et al. .................. 297/392 X |
| 3,679,295 | 7/1972 | Newman et al. ................ 351/7 X |
| 3,724,932 | 4/1973 | Cornsweet et al. ................ 351/7 |
| 3,940,846 | 3/1976 | Grenon ........................... 357/17 |

OTHER PUBLICATIONS

Floyd, "On the Line of Sight", Design, Apr. 1959, pp. 24–31.

Primary Examiner—John K. Corbin
Assistant Examiner—John D. Lee
Attorney, Agent, or Firm—Haseltine, Lake & Waters

[57] ABSTRACT

A portable device for accurately measuring horizontal and vertical movements of each eye of a subject by reflecting thereon non-modulated invisible infrared light and converting the movements into continuous voltages. The device comprises emitters and detectors, arranged in a fixed spaced relationship and mounted rigidly either on a helmet worn by the subject, a head clamp holding the head immobile, or a separate support outside the subject.

9 Claims, 18 Drawing Figures

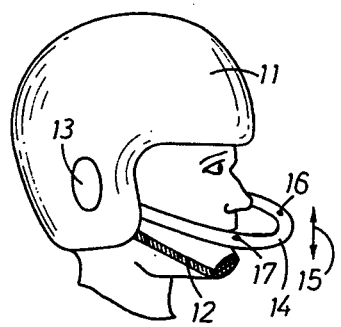
Fig.1.
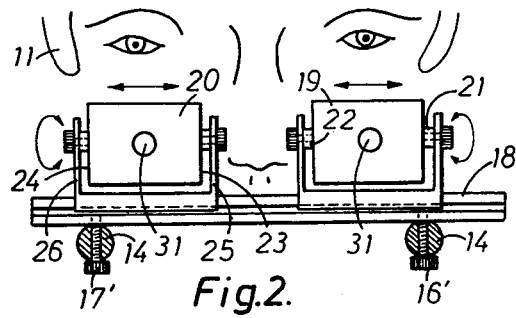
Fig.2.
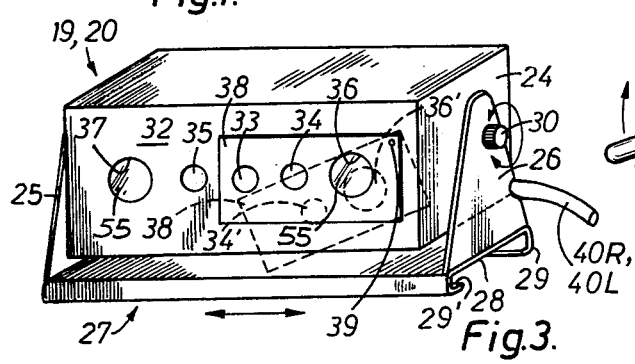
Fig.3.
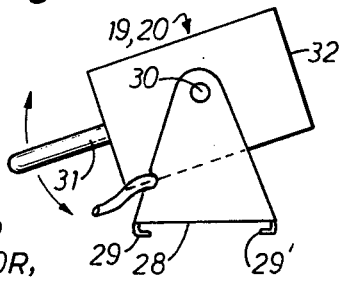
Fig.4.
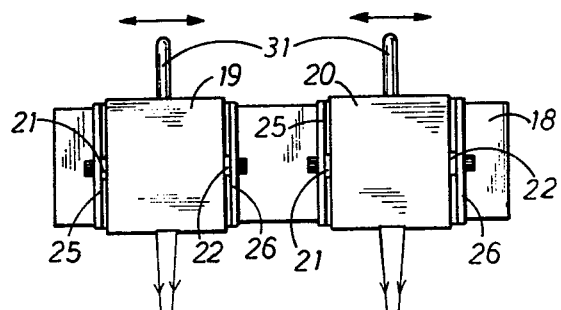
Fig.5.
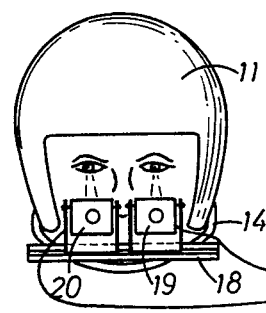
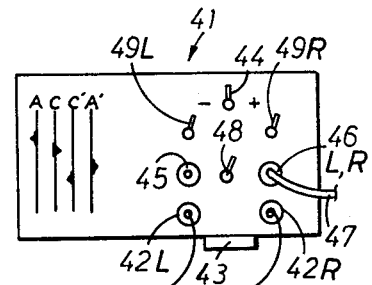
Fig.6.

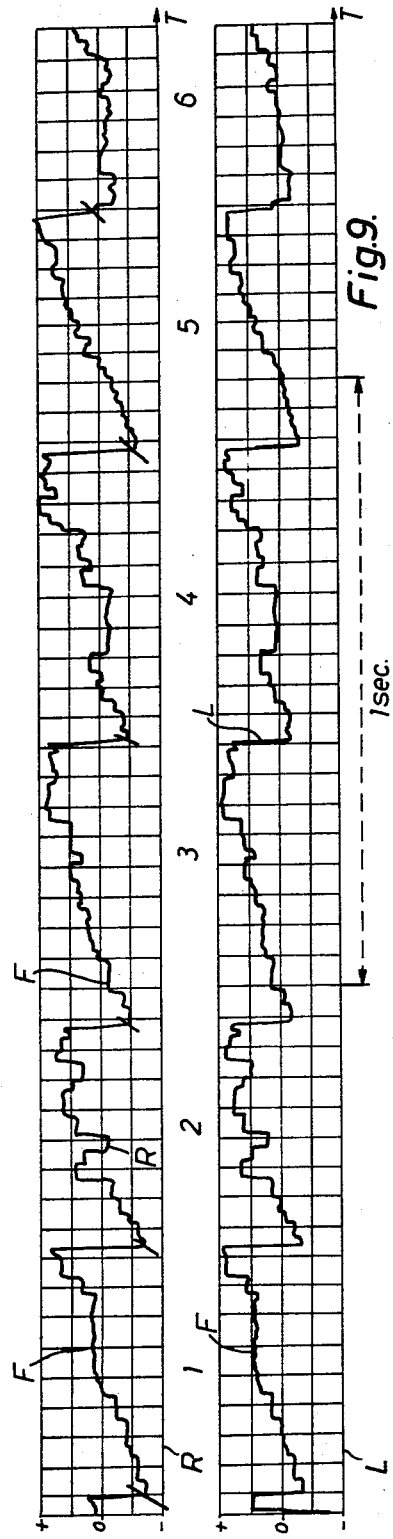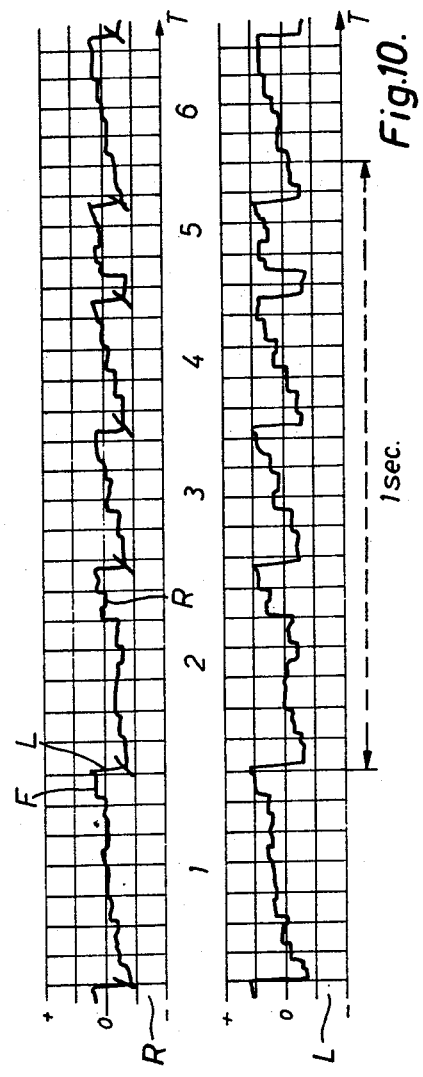

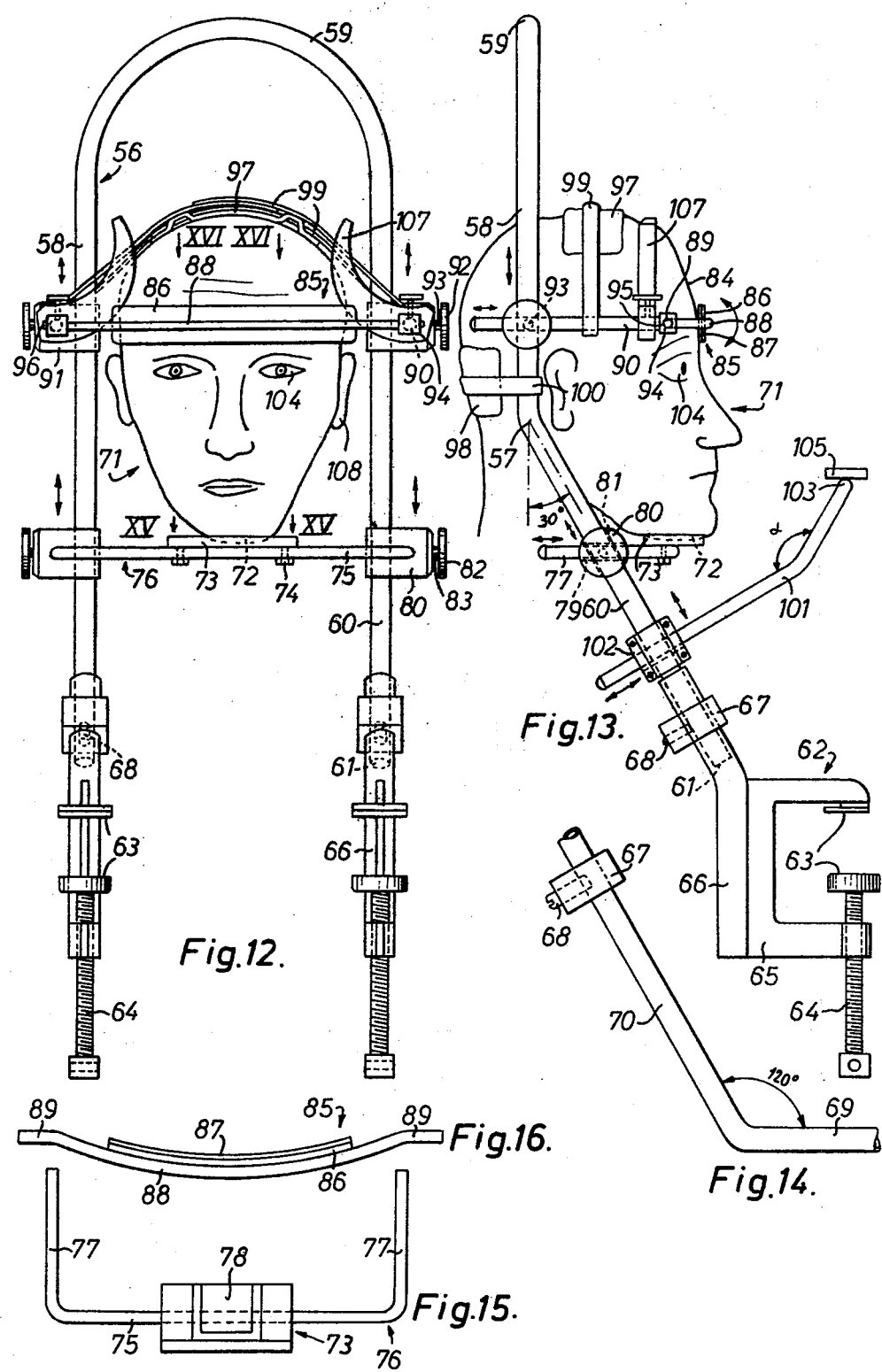

PORTABLE DEVICE FOR THE ACCURATE MEASUREMENT OF EYE MOVEMENTS BOTH IN LIGHT AND OBSCURITY

FIELD OF THE INVENTION

The invention relates to a portable device for the accurate measurement of voluntary or involuntary eye movements of a subject both in light and darkness by means of an optical system comprising at least one beam of invisible infrared light directed towards the eye and a fraction of said beam reflected on the eye, the length of each incident beam remaining constant during the measurement.

The observation of these movements has been of paramount interest for a long time because it can provide means for correcting defects of eyesight and reveal physiological abnormal conditions; thus a nystagmus, which consists of spontaneous oscillatory short and jerky movements of the eyes, often indicates a disease of the cerebellum.

BACKGROUND

According to earlier methods, electrodes were applied to the head to reveal the extent of stretching and contraction of the muscles of the eyes when they move so that the amplitude of eyeball movement can be determined, but these methods are delicate to perform and they have only a limited scope.

In order to overcome these shortcomings, differential photoelectric nystagmagraphic instruments using visible light were built separately by Prof. N. TOROKS, University of Illinois, Chicago, USA (1951, 1955) and by C. R. PFALTZ and H. R. RICHTER who recorded nystagmus to 0.1 of a degree (*International Review of Otolaryngology*, Vol. 18, No. 4, 1956, New York). The method works on the principle that the sclera (i.e. the white of the eye) is a much better light reflector than the iris (i.e. the transparent portion of the eye). Thus, photocells were placed so that their medial edges aiming at the medial and lateral junctions of the cornea and iris respectively with a source of central light interposed centered on the pupil, would lead to an intensity variation of the light reflected by the eye's surface.

The intensity variations can be picked up differentially by 2 or 4 photocells mounted, for example, on goggles and are led to a current EEG recorder. Using 4 photocells, the eye movements both in a horizontal plane and a vertical plane can be recorded simultaneously by 2 channels of the recorder. The magnitude of the recorded nystagmic jerk was found to be proportional to the eye movement and its linear increase was proved. The method is technically simple, its sensitivity is high and it can be used for recording spontaneous caloric, rotational, galvanic as well as positional nystagmus.

In the course of 8 years, these authors improved the method; they replaced the visible central illumination by invisible infrared light centered on the pupil to eliminate the effect of light adaptation and irritation and consequently rapid tiring of the subject. (*Annals of Otology, Rhinology and Laryngology*, Vol. 73, No. 4, page 893, December 1964). Thus a nystagmus jerk as small as 0.5° could be accurately measured; there is a linear increase in the amplitude of the recorded spikes up to an eye movement of 20°, which exceeded the limits found in clinical nystagmus.

Such a principle was also applied by NASA in the space program (*NASA Tech Brief* 65-10079, March 1965): a device whereby an astronaut, precluded from using his hands, is capable of starting an external relay from a distance simply by voluntarily moving the eyes. The device, mounted on an eyeglass frame, includes a source of infrared light and a cadmium selenide detector fixed on the frame in such a way that, when the astronaut gazes straight ahead, the full power of the radiation infringes on the sclera on one side of the iris, and is reflected upon the detector; if, however, the astronaut deliberately turns the iris to the incident infrared beam, most of the power is absorbed and the controlling external relay closes, thereby setting out a predetermined sequence of operations.

The prior art also comprises a known device patented in 1969 (U.S. Pat. 3,473,868), consisting of an eyeglass frame which carries in front of each eye a modulated infrared radiation emitter and a pair of detectors, the circuit of the detectors measuring either the horizontal or the vertical displacements of an eye as a function of the variable reflecting power of the regions submitted to the incident radiation.

In practice however, this device is less satisfactory than simpler arrangements proposed by PFALTZ et al. Thus, the accurate setting of minute emitters and detectors is laborious and tedious and the whole operation has to be repeated every time the frame moves during testing and examination. Moreover, the proximity of objects close to the eyes is psychologically disturbing for the patient even if he is not dazzled; also, since the measurements have to be carried out in darkness to prevent troublesome interferences, the utility of the device is limited to experiments where the target of the eyes is only weakly lit, such as, the examination of reading power for example.

Finally, by virtue of the fact that the infrared light is modulated, the output signal only corresponds to an average of the positions of the regions submitted to illumination and not to the instantaneous state of said positions.

Further, as is well known, modulation invariably causes a delay of the corresponding signal, i.e. it is not fully on line, whereas a non-modulated system is. This is of course of considerable importance to certain types of measurements.

SUMMARY OF THE INVENTION

It is an object of the present invention to remedy these drawbacks in fields where ocular movement measurement is currently applied now, such as the exploration, either of the horizontal or the vertical movements of one eye or both eyes in nystagmus, reading power, etc. by carrying out said measurement continuously and more accurately, not only in darkness but also in light using a non-modulated infrared source to illuminate the eyes.

It is another object of the invention to apply said measurement, as carried out under the conditions defined above, to the simultaneous exploration of both horizontal and vertical components of a nystagmus in one single eye of a subject who has only one eye functioning adequately for the purpose of the examination and diagnoses to be made, the other eye of the subject being either missing, blind or otherwise inoperative for said purpose, or functioning for purposes of comparison; the same measurement can be carried out on both eyes simultaneously.

It is yet another object of the invention to apply to said measurement, as carried under the conditions defined in the first object, to obtain objective measurement of resistance to glare, of recovery from eye blinding, of visual acuity and of any other determining factor of eyesight that may be required in medical or fitness tests.

The device according to the invention comprises, for each eye of a subject, emitters and detectors of non-modulated infrared light as constituent elements of an optical system, with infrared filters and a source of visible light which can be obturated, to suitably direct on the eye each incident beam of the light radiation, the constituent elements being arranged in fixed spaced relationship so as to form a distinct electro-optical set which is screened and is mounted either in the field of vision of the subject or outside said field, and which is connected to an electronic circuit provided with a source of direct current and optionally with a voltmeter, said circuit being capable of converting analogically into a continuous voltage or output signal the power of reflected radiation of the optical system, said voltage or output signal being received constantly by peripheral apparatus capable of processing, reading and/or recording said signal.

According to the invention, the emitters of each electro-optical set, which are mounted in series, are photoluminescent diodes capable of producing a beam of well defined power, and the two sets for the left and the right eye respectively are subjected to a voltage of inverse polarization under constant current.

The detectors of a set are photoelectric cells, highly sensitive to reflected infrared light, which are inserted in the electronic circuit of the device.

According to a first embodiment of the invention, wherein the device is suitable only for the exploration either of horizontal or vertical ocular movements using one eye or both eyes, the set for each eye comprises three electrically screened emitters mounted in a horizontal line, the central emitter constituting a source of visible light which can be mechanically obturated and the outer emitters being each capable of directing onto the eye a non-modulated beam of invisible infrared radiation which can be reflected thereon, a fraction of said reflected radiation being available for reception by two corresponding detectors disposed at either end of the line of emitters.

According to said embodiment, the electronic circuit of the device optionally comprises means known per se for switching off the central emitter so that the orienting visible light is extinguished electronically instead of mechanically as soon as the emitters have been correctly directed onto the eyes.

According to a second embodiment of the invention, wherein the device is suitable for the simultaneous exploration of all movements of at least one eye, each set comprises, besides the five electronic elements disposed in a horizontal line corresponding to the first embodiment, four additional electronic elements disposed in a vertical line, respectively an emitter at either side of the central emitter of said horizontal line and a detector at either end of said vertical line.

According to the latter embodiment, the electronic circuit of the device comprises means known per se for cancelling out vertical interference on horizontal measurements and respectively for cancelling out horizontal interference on vertical measurements so that relatively pure horizontal and vertical eye movement response is respectively obtained.

The electronic circuit comprises potentiometers for calibrating the output signal depending whether the subject gazes ahead or makes respective maximum horizontal or vertical ocular displacements.

According to one embodiment of the invention, the device comprises a helmet firmly secured on to the head, a portable control unit and peripheral apparatus, the helmet possessing a fixed bar which enables one to mount the electro-optical sets in a regulatable manner both in height and in width, either in the visual field of the subject or outside said field, in order to carry out measurements either in light, or in darkness, the control unit comprising a source of direct current and various electronic assemblies for calibrating purposes with switches and sockets, including one for connecting to the peripheral apparatus and optionally a voltmeter.

As a variant of the preferred embodiment, the device comprises mechanical means for making the subject's head integral with a stable or other basically mobile or immobile object, such as an armchair fixed on the floor, a major heavy instrument such as a revolving nystagmus system or chair or seat fixed into a vehicle, while the constituent elements of the optical systems and the components of the electronic circuit with their accessories are mounted in fixed fashion at the required position for carrying out the measurements.

Advantageously, said mechanical means are rigidly connected to the constituent elements of the optical system.

BRIEF DESCRIPTION OF THE DRAWINGS

The appended drawings represent by way of examples several embodiments of the invention wherein FIG. 1 shows a subject wearing an American football helmet with chin strap and mouth protecting round bar, said bar being destined to fix electro-optical elements in accordance with the invention;

FIG. 2 shows a horizontal grooved plate screwed on two opposed positions of the round bar to which are fixed two prismatic housings which constitute electro-optical sets containing five elements disposed in a horizontal line;

FIG. 3 represents one of said electro-optical sets with its support, as it is seen by the subject;

FIG. 4 is a side view of the set of FIG. 3;

FIG. 5 is a schematic plan view of the apparatus in FIG. 2;

FIG. 6 is an overall schematic view of a device with helmet and electro-optical sets, the sets being connected to a portable unit which contains the electronic components designed to provide an output signal corresponding to the displacements of the subject's eyes;

FIGS. 9 and 10 represent graphs obtained with the device in reading exercises;

FIG. 12 is a front view of a head fixture or clamp connected rigidly to a table clamp;

FIG. 13 is a side view of the fixture of FIG. 12;

FIG. 14 is a side view of an attachment, integral with an instrument, for rigidly connecting the head fixture to said instrument;

FIG. 15 is a top view of the chin support of the head clamp taken along lines XV—XV in FIG. 12;

FIG. 16 is a top view of the forehead rest of the head clamp taken along lines XVI—XVI in FIG. 12;

DETAILED DESCRIPTION

Figure 7:
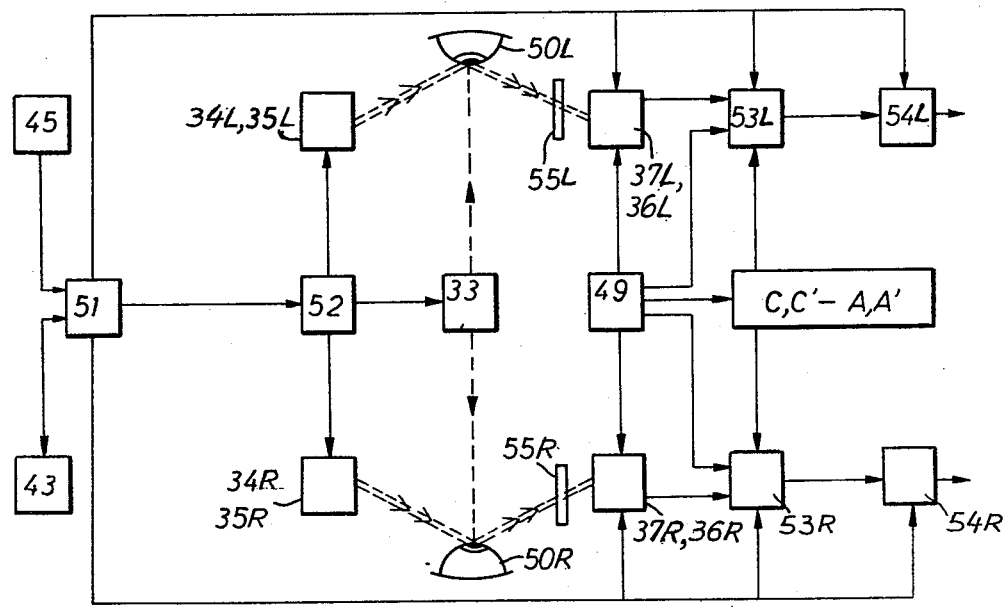
FIG. 7 is a block diagram of the device.

The helmet 11 (FIGS. 1, 6), provided with a chin rest 12 and with openings 13 in order to free the ears is supplied with a round bar 14 (normally for the protection of the mouth) which is fixed laterally to the helmet. The round bar has two holes 16 and 17 through which the base of a horizontal grooved plate 18 can be fixed by means of screws 16' and 17' (FIG. 2).

Two prismatic electro-optical sets 19 and 20 (FIG. 2-6), advantageously screened, are pivotally mounted with tight fit by means of discs 21 and 22 wedged between the side walls 23 and 24 respectively of the sets and the uprights 25 and 26 of a U-support 27 (FIG. 3), the latter having at the bottom 28 two extended angle pieces 29, 29' to hold the upper part of the grooved plate 18 (FIG. 2). A screw 30 (FIGS. 3, 4) which passes through upright 25 and is screwed in disc 21, makes the set integral with U-support.

Each set can be angularly adjusted by means of a rod 31 mounted at the rear side, as shown in FIG. 4; thanks to the angle pieces 29, 29', which constitute tight fit guides, the set can also be adjusted in width along the grooved plate (FIG. 2-6), so that face 32 (FIG. 3) of each set is placed exactly in front of the subject's eyes where it is required.

In the center of said face 32 there is an opening 33 through which a beam of visible light can be directed to the eye; on either side of said opening there are two openings 34 and 35 to allow two invisible beams of infrared to pass and, at the outer sides, two other openings behind which are mounted two detectors 36 and 37 for detecting non-modulated infrared reflection. An opaque plate 38, susceptible of rotating with tight fit about a pivot 39 and having openings 34' and 36' corresponding to openings 34 and 36 is in front of the openings 34 and 36 when a measurement is carried out, the opening 33 being obturated by the plate.

Before commencing operations, it is ascertained that the incident beams of non-modulated infrared light issuing from emitters 34 and 35 fall exactly on the eye when the subject gazes straight ahead. To this effect, in the case of the measurement of horizontal movements of an eye, the source 33 of visible light is uncovered by shifting plate 38 downwards; the electro-optical set or housing is then moved in width and elevation until the incident beam of visible light falls on the pupil of said eye, then opening 33 is obturated by moving plate 38 up and in front of it.

In order to carry out a measurement in the vertical mode, the housing is shifted along the grooved plate towards either the left (for the right eye) or respectively towards the right (for the left eye) until the visible spot is in the corner of the eye.

In the case of the left eye, for example, emitter 34 now directs a beam of non-modulated infrared radiation on to the iris and the incident beam from emitter 35 falls outside the eye lid. In the case of the right eye, it is the emitter 35 which irradiates the iris, the incident beam from emitter 34 falling on the skin.

Of course, as in the case of measurements in the horizontal mode, the source of visible light is obturated after positioning so that the eye is no longer illuminated.

It is worth pointing out here that the above adjustment procedure for the accurate measurement of vertical movements is only strictly valid provided the eyelids are sufficiently apart when the subject opens his eyes. If however only a narrow crescent of eye surface is revealed the visible spot must be shifted to the edge of the eye exactly where the lids come together but neither above nor below them.

The electro-optical set for the left eye and that for the right eye possess a respective cable 40L and 40R (FIG. 3, 4, 6) wherein are gathered screened leads connected to the emitters and detectors; these cables terminate with plugs adaptable into corresponding sockets.

FIG. 1, 2 and 6 show a subject with helmet 11 equipped with electro-optical sets 19, 20 arranged outside the normal visual field. It is clear however that said sets can be moved with respect to the subject's eyes in any appropriate manner; thus a bridge (not shown in the drawings) may be mounted upon the round bar 14 in such a manner that the grooved plate 18 is just below the theoretical line joining the eyes.

Plate 18 may advantageously be provided with means for fixing an easel on which is placed either a text or a pattern to be read or examined by the subject. One of said patterns comprises straight lines enabling the operator to determine accurately both the center of the eyes when the subject gases ahead and the amplitude of vertical and horizontal deflections of each eye; this includes the precise degree of movement using a target appropriately lined.

The inventive device includes a portable control unit 41 which contains the electronic elements, assembled according to the circuit diagram (FIG. 8) whereby the displacements of the eyes can be converted analogically into a continuous voltage; the sources of electric supply of the circuit are electromotive sources VEE and VCC, advantageously of +12 V and −12 V, obtained either by rectifying the local supply circuit, or by means of autonomous and re-chargeable accumulator-batteries or by powerful DC batteries such as used on vehicles.

Figure 8:
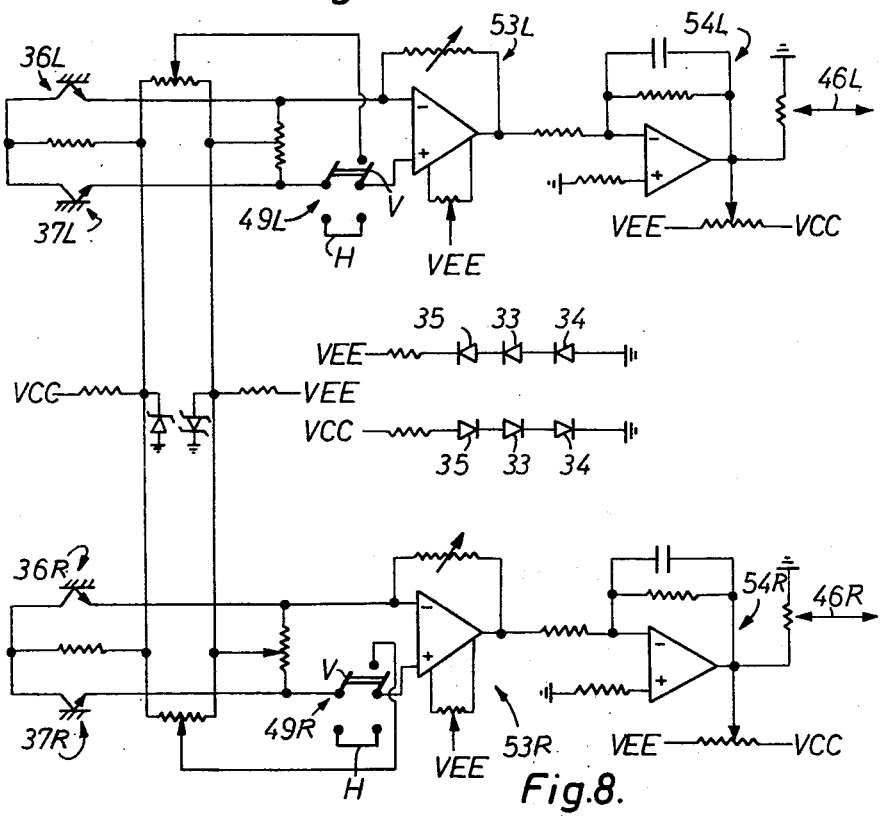
FIG. 8 is a circuit diagram of the device.

The portable unit is equipped with the following elements (FIG. 6):

two sockets 42L and 42R capable of receiving cables 40L and 40R respectively, a voltmeter 43 which permits one to check the adequacy of charge of the batteries where used, by turning a switch 44 either to the left or to the right;

a socket 45 which can receive corresponding plugs of the sources of electric supply for the circuit but which is closed by an electrically inert plug when the device is fed by batteries (housed in the case); the socket can be used to connect the supply system to a recharge unit;

alternately the power supply may, instead of batteries, be an electric main line, the autonomous electric supply of an automobile (an ambulance for exemple) or any other supply. In this case socket 45 is replaced by a colored "power-on" light.

a socket 46L-R, where the output signal of the electronic circuit of each respective set is present; by means of a lead 47 connected to said socket, every signal can be transferred to peripheral apparatus (pen - or tape-recorder, oscilloscope, etc.);

an on-off-charge switch 48 to start and stop the device, or to recharge the batteries;

two switches 49L and 49R, one for each eye, to establish measurement either in the vertical mode V or in the horizontal mode H (FIG. 8);

bars C, C' and A, A' (FIG. 6) having each a slider to calibrate the device, viz. to alter the amplitude of the signal, first in order to center it when the subject gazes straight ahead, and later in order to calibrate the signal so that the degree of deflection of the eyes is compatible with the deflection required.

In the circuit diagram (FIG. 8) are shown the constituent elements of the optical system together with the electronic components of the circuits necessary for converting infrared reflections into continuous voltages. In this circuit diagram the letters L or R have been added to the reference numerals already mentioned, in order to indicate whether the referred part belongs to the left of right electro-optical set. Obviously a source of visible light can be produced in any known manner. In the present embodiment of the invention represented in the drawings, the source is a diode 33 (L, R) inserted in a circuit of infrared light emitting diodes and the emitted visible light is advantageously red since for the same amount of power output, red color is most easily visible to the human eye.

The functions of the various elements of the device are schematically summarized in the block diagram (FIG. 7), where the left and right eye 50L and 50R, have deliberately been shown turned towards each other to simplify the drawing.

Besides the functions already mentioned before, the black diagram also has boxes 51 to 55 which designate the following:

51: the electric supply;
52: adaptation for infrared emitters;
53: pre-amplification;
54: sense and filtering amplification adaptation;
55: optical filtering for infrared radiation i.e. a filter adapted to pass only infra-red radiation.

The box C, C' – A, A' designates positioning and gain control and box 45 represents the control of charge or utilization function.

The device has the following technical specifications:

| | |
|---|---|
| RESOLUTION | Horizontal +/− 1/4° |
| | Vertical +/− 3/4° |
| ACCURACY | Horizontal 1/2° |
| | Vertical 1° |
| SENSITIVITY | Horizontal 15 mV/degree-min. |
| | Vertical 10 mV/degree-min. |
| DRIFT OF OUTPUT SIGNAL | 8 millivolt/hour |
| DEFLECTION | Horizontal +/− 60° |
| | Vertical: upward 25° downward 60° |
| POWER SUPPLY | + 12V, −12 V rechargeable accumulator - batteries with charge controlling voltmeter and charging unit. Optionally power line or 12V-batteries (automobile, etc.) |
| OUTPUT VOLTAGE | +/− 12 V max |
| OUTPUT IMPEDANCE | 50 ohm - 1 Megohm |

It is important to stress that, contrary to what happens in devices relying on modulated infrared radiation, the response of the circuit according to the invention is constant and as a result the ocular movements can be monitored and recorded without danger of interfering frequencies from other instruments.

It will be observed also that thanks to the device the full deflections, both vertical and horizontal, can be followed.

Moreover it may be worth mentioning that the weight of the helmet, together with its electronic controls and a battery charger (in the case of an autonomous device) is less than 5 kg, and that whole instrument set is not bulky.

Furthermore, the helmet 11 may be equipped with a cine-or TV-camera adapted to film the scenery seen by the subject while either a peripheral apparatus simultaneously records the movements of one eye in the horizontal mode and the other in the vertical mode (exploration), or said recorded signal is incorporated in the video camera.

Thanks to the high stability of the optical system, wherein the emitters and detectors are placed in a fixed spaced relationship, measurements can be carried out accurately and the output signals will always be independent of whether the subject's head is free to move (helmet system) or not, i.e. the head is held in a fixed position (clamp system to be described presently). These signals are obviously independent also of whether the subject is made to follow a target with the eyes or, alternately, the subject sits on a revolving chair while nystagmus movements are determined in total darkness, or otherwise.

The invention can be illustrated with a reproduction of graphs, in rectangular coordinates, corresponding to the horizontal recording of the eyes of two children during reading exercises (FIGS. 9, 10). The letters R and L stand respectively for the right and left eyes, the time T is given by the abscissa and the output signals of the electronic circuit, measured in millivolts, are in positive or negative ordinates respectively from the center O between the left margin of the text (lower line of the graph) and the right margin (upper line).

The shape of the graph for a dyslexic child (FIG. 9) and for a normal child (FIG. 10) having different distribution of the time spent going back to the left margin L, in fixations F and in reading regressions R either in the case of a dyslexic (FIG. 9) or respectively a normal child (FIG. 10), shows among other things that the former has required nearly twice the time to decipher six lines of text. These results, which are of interest chiefly to psychologists and pedagogues, may also reveal brain abnormalities.

The device also permits, as opposed to existing instruments permitting only subjective measurements, objective measurement of resistance to glare, recovery from temporary blinding, of visual acuity and of any other determining factor of eyesight that may be required in medical or fitness tests. This type of measurement is of paramount interest when it is proposed to check the visual aptitudes of drivers, pilots, etc.

The principle applied in some of these is the recording of the eye movements of the subject while following a target which can be a rotating or oscillating object and the recording would automatically show when the subject is no longer able to follow the target, or can follow it again.

As regards exploration of a moving scenery, using the said prismatic housings containing five electro-optical elements arranged in a horizontal line, it was found however that the signal obtained in one functioning mode, e.g. the horizontal is too greatly influenced by the simultaneous vertical movements of the same eye; the same applies to the signal obtained in the vertical mode of the other eye, i.e. the signal is too greatly influenced by the simultaneous horizontal interference thereof, as the output signal of any eye does not contain solely the horizontal or vertical movement but also components of both movements.

This can be expressed thus:

$H'_L = H_L + v_L$ and $V'_R = V_R + h_R$, where L and R refer to the left and right eye respectively, H' and V' are the signals actually recorded, H and V represent the respective major contributions to the corresponding signals, and $h$ and $v$ the contributions due to interference in the opposite mode of functioning.

Depending on the shape of the eye-ball and other factors, the final output signals may not be sufficiently pure to ensure accuracy and reproducibility of the results. Moreover, if the subject has only one eye functioning adequately for the purpose of exploration, these examinations cannot be performed at all. In addition, the invention therefore includes means for obtaining relatively pure horizontal and vertical signals simultaneously from a single eye, the effect of interfering components being reduced to a minimum by suitably electronically adding or subtracting from H' and V' the necessary fraction of the opposite signal.

Figure 11:
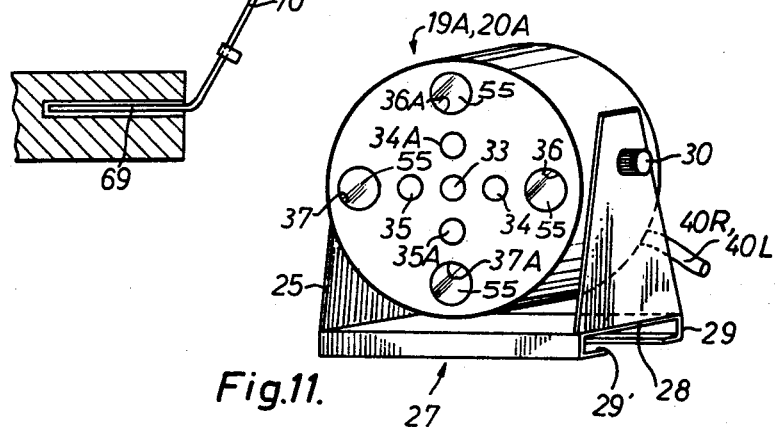
FIG. 11 illustrates one of two cylindrical housings which constitute electro-optic sets containing nine elements arranged in a cross relation to determine simultaneously both horizontal and vertical ocular movements in a single eye; once mounted said housings appear the same as in FIGS. 2, 4, 5 and 6.

An improved electro-optical set, 19A, 20A (FIG. 11) capable of fulfilling this purpose contains, besides the elements already described (5 elements in horizontal line), four additional electronic elements disposed in a vertical line, respectively an emitter 34A, 35A at either side of the central emitter 33 of said horizontal line and a detector 36A, 37A at either end of said vertical line, the above additional elements being mounted exactly in the same manner as in the horizontal row, conveniently in a cylindrical housing.

The adjustment procedure before commencing any eye movement measurement with said cylindrical housing 19A, 20A (FIG. 11) is the same as with a prismatic five element electro-optical set 19, 20 (FIG. 3)

In the cylindrical housing no obturating plate is used because the visible light can be electronically extinguished; clearly the same means can be applied to the prismatic housing. Needless to say, the portable control unit 41 (FIG. 3) is to comprise additional parts known per se to operate both the electronic switch of emitter 33 and elements 34A-37A.

It is obvious that both prismatic sets 19, 20 and cylindrical housing 19A, 20A can be mounted not only on the round bar 14 (FIG. 3) of a type of helmet 11 referred to, but also on any other suitable support such that the eyes and the electro-optical elements respectively are maintained in fixed spaced relationship.

Said support or head clamp is conveniently by way of example, a hollow or solid rigid metallic inverted U-tube 56 (FIG. 12 and 13) of circular section having advantageously a diameter smaller than 10 mm (head fixture).

The distance between the branches of the U-tube is greater than the maximum distance between the ears of a person, so that the head can pass freely inside the fixture. A bend 57 (FIG. 13) is made conveniently near the mid-point of the structure whereby the upper part 58 (FIGS. 12, 13) of the structure, including the curved portion 59, extends vertically well above the head while the lower part 60 is inclined about 30° with respect to the plane of the vertical part and lies above the level of the chest with the ends 61 pointing downwards.

In a first embodiment of the head clamp which is designed comfortably to fix to a table, for example, the head of a person sitting near the table, a double clamp 62 with jaws 63 is tightened to the table by means of conventional screws 64. On the vertical cross pieces 65 joining each set of jaws are fixed tubes 66 with a bent part inclined towards the ends 61 of the branches. The internal section of tubes 66 is wider than that of branches and each tube is provided with a locking device 67 including a screw 68. By engaging the ends of the branches into the tubes and tightening the screws the U-tube structure is rigidly fixed to the table.

In a second embodiment of said head clamp, the structure is made integral with an instrument placed on a table or similar support. To the instrument are fixed two parallel essentially horizontal tubes 69 having the same internal section as that of tubes 66 (FIG. 14) of the first embodiment, the pipes having their ends 70 inclined (for instance at 120°) in the same direction as the ends 61 of the U-tube structure and being provided with a locking device 67 including a screw 68 analogous to that of the first embodiment. On engaging the ends of the branches into the ends 70 of the parallel tubes 69 and tightening the screws, the U-tube structure is fixed rigidly to the instrument.

In all that follows it is to be understood that the expression "head clamp" shall cover both embodiments although there may be no clamp present at all.

Moreover, in the case of the first embodiment, the end 61 of the inclined branches 60 of head fixture 56 may be fixed in any suitable manner to any stationary object. Thus, said object may be the arms or sides, for example, of a seat occupied by the person fitted with the said fixture, the arms possessing fixed tubes 66 or any manner of cavity for fixing the ends 61 therein; alternately, the tubes 66 or cavities may be connected to any stationary object such as the floor, a wall, a panel, etc.

The head fixture being rigidly connected as described above, it is necessary to hold the head 71 immobile with respect to said fixture; for this purpose the fixture must comprise means for supporting the chin and pressing against the forehead, together with means for strapping the top and back of the head.

In order to support with comfort the chin 72 (FIGS. 12, 13 and 15) of the person, a rectangular slab 73 of resilient material adhered to a plate is fixed horizontally by screws 74 in the middle portion 75 of a straight angled U-tube 76 obtained by twice bending a straight tube, the lateral sides 77 of the U-tube being connected horizontally to the parallel inclined branches 60 of the head fixture 56.

The slab 73 of resilient material is advantageously hollow in the middle 78 and the cavity may be filled with a soft material, for instance an expanded polyurethane, so that the chin may depress the slab yet be held firmly and without discomfort.

Each side tube 77 (FIG. 12 and 13) of the chin-support 76 is able to pass horizontally through a cylindrical channel 79 drilled in a solid boss 80, conveniently of Bakelite, which also possesses a second channel 81 inclined in the direction of branch 60. Thus the two bosses can travel up and down the branches and the side tubes can be moved horizontally forwards and backwards as shown by the double arrows in FIGS. 12 and 13 so that the resulting position of the chin-support can be adjusted; on screwing a knob 82 threaded internally at 83, the position can be made permanent.

The head of the person can be positioned with any desired angle of tilt by suitably pressing against the forehead 84 using a forehead-rest 85 (FIGS. 12, 13 and 16).

The latter consists of a curved blade 86 (FIG. 12) provided on the concave side with a sheet 87 of resilient material in order to follow substantially the profile of the forehead. The blade is fixed to a correspondingly curved tube 88 terminating at the opposite ends with two axially straight ends pieces 89 to be mounted horizontally on two tubes 90 placed horizontally on either side of the vertical branches 58 of the head fixture.

The level of each tube 90 and the position of forehead rest 85 with respect to the plane of the head fixture 56 are controlled by means of a boss 91, similar to bosses 80, having a knob 92 with internal thread 93 and possessing two channels at right angles, in order to move the boss up and down and the horizontal tube 90 forwards and backwards as shown by the double arrows in FIGS. 12 and 13.

The front end of each horizontal tube 90 is capped with a hollow member 94, conveniently in the form of a cube of hard plastic material, which is provided on one side with a cavity 95 to rotatably receive straight end 89 of the forehead rest 85. In this fashion the forehead-rest can be made to swivel as indicated by the curved double arrow (FIG. 13) to follow the slope of the forehead at any level. A screw 96, mounted in the hollow member 94 opposite the cavity 95, is used to permanently fix the tilt of rest 85 when the correct level of tubes 90 has been made permanent by screwing the knobs 92.

The positions of the chin-support and the forehead-rest having been selected, it is now necessary to hold the top and the back of the head in a fixed position by means of broad flaps, suitably of leather or equivalent flexible material, each attached by a strap to tubes 90 and to the branches of the inverted respective U-tube. This is shown schematically in the drawings where the reference numerals 97 and 98 designate the top and back flaps respectively, 99 and 100 the corresponding straps.

Each flap is substantially rectangular. Two internal narrow bands crossing its longitudinal axis are formed by cutting slots in it so that the strap, passing under the bands, can be attached to the fixture. The attachment is made by looping the strap over each tube and clipping it. The strap is much longer than the distance between the points of attachment and therefore there is an extra length beyond each point, the two extra lengths are then brought towards each other in overlapping relation to make a taut continuous strap and this is applied to the flap. The three superimposed strap layers are held firmly in position by a suitable fastener (VELCRO, Registered Trade Mark).

Figure 17:
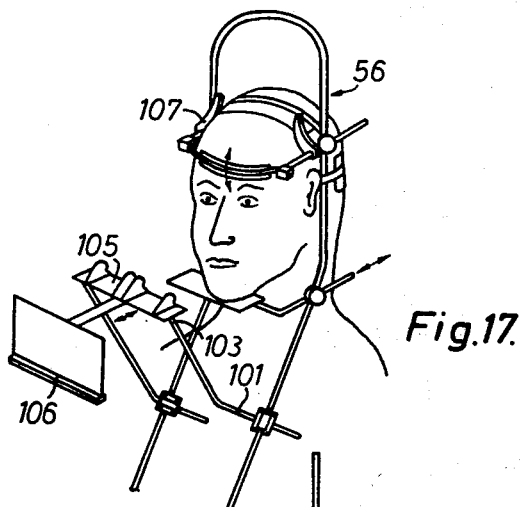
FIG. 17 is a diagrammatic illustration of the head fixture.
Figure 18:
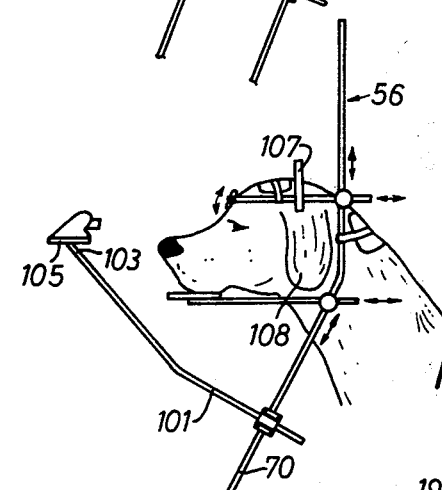
FIG. 18 is a side view diagrammatically illustrating a head fixture mounted on a dog and connected to an apparatus.

The prismatic or cylindrical housings 19, 20 or 19A, 20A respectively designed for the accurate measurement of the eye movements may be mounted on the head fixture (FIGS. 13, 17 and 18).

The two lateral branches 101 (FIG. 13) or a right angled U-tube are clipped to the branches 60 of the head fixture by means known per se 102, the branches 101 having been bent at an angle α so that the horizontal middle portion 103 is located at the correct distance from the eyes 104 for the measurement.

The electro-optical device (FIGS. 17, 18) is mounted on a horizontal plate 105 (FIG. 13) fixed to portion 103.

It is clear that minor adjustments can be made by moving the clipping means up and down along tubes 60 and the U-tube 101 forwards and backwards with respect to the plane of fixture 56 as shown by the double arrows.

The electro-optical device itself can be tilted appropriately towards the eyes.

Furthermore, as the head clamp, fitted with the U-tube structure 101 - 102 - 103 is absolutely rigid, additional attachments can be fitted thereon (FIG. 17) such as a support 106 for reading matter located at the correct distance from the eyes.

Of course the head fixture 56 may also be equipped with temple-horns 107 (FIGS. 12, 13, 17) slidably fixed on tubes 90 by means of bosses analogous to bosses 80 and 91, the temple-horns being normally used in the art of eye movement measurement.

It is noteworthy that the head fixture 56 leaves the ears 108 free. This is extremely important for any medical examination of the ears and also for the determination of involuntary eye movements, called nystagmus, which can be induced by the introduction of liquid in the ears.

Finally the equipment of the head clamp according to the invention can be adapted to fit the head of animals such as cats or dogs, for example, (FIG. 18) so that tests or minor surgical head operations can be carried out while the animal is conscious.

The advantages of the head clamp (sturdiness, versatility in use, etc) over the prior art devices are obvious from the above description. In addition, the units of the head clamp are cheap to produce, easy to carry by hand and simple to assemble.

I claim:

1. A device for measurement of movements of an eye of a subject comprising support means for engaging the head of a subject in fixed relation therewith, a housing mounted on said support means at a fixed distance from the eye of the subject, two non-modulated infra-red light sources in said housing positioned to direct infra-red beams of light onto the eye of the subject, two sensing means in said housing equally spaced from said sources along a straight line therewith for receiving infra-red light reflected from said eye by the corresponding sources, said sensing means and said light sources being in fixed relationship in said housing, each of said sensing means including an infra-red light filter to pass substantially only infra-red light, said housing having an opening located in the center of the line joining the sources and the sensing means and through which opening a beam of visible light can be directed towards the subject to permit the irradiating infra-red light to correctly fall upon the eye before commencing an operation, means for selectively interrupting said visible light, means for calibrating said housing on said support means for controlling the positioning of said beams from said sources to the eye and thereby the reflected beams from said eye, and non-modulated electronic means connected to said sensing means for producing an output signal, said calibrating means permitting lateral sliding movement of said housing along an axis parallel to said line joining the sources and sensing means and pivotal movement of said housing along an axis parallel to said line.

2. A device as claimed in claim 1 wherein said light sources and said sensing means are disposed on said line for responding to one linear movement of the eye.

3. A device as claimed in claim 2 wherein two of said housings are disposed on said support means, each housing being operative with a respective eye.

4. A device as claimed in claim 2 wherein two further light sources and two further sensing means are disposed on a line perpendicular to said line with the first two light sources and two sensing means thereon.

5. A device as claimed in claim 4 wherein said light sources and sensing means are arranged symmetrically on their respective lines and said lines intersect at a common center, said source of visible light being at said center.

6. A device as claimed in claim 1 wherein said support means comprises a helmet affixable onto the head of the subject, and a rigid bar on said helmet for support of said housing.

7. A device as claimed in claim 1 wherein said sensing means includes means for analog conversion of the sensed infra-red reflected light into said output signal.

8. A device as claimed in claim 1 wherein said support means comprises a rigid first U-tube structure including branches which lie behind the ears of the subject, a curved portion above the head of the subject, said branches having ends inclined toward an object to which said structure is to be secured, supports for the chin and the forehead and flaps secured by straps to hold the top and back of the head of the subject.

9. A device as claimed in claim 8 wherein said support means further comprises a second U-tube structure adjustably secured to the first U-tube structure and projecting in front thereof.

* * * * *